United States Patent [19]
Leunbach

[11] Patent Number: 5,263,482
[45] Date of Patent: Nov. 23, 1993

[54] THERMOGRAPHIC IMAGING

[75] Inventor: Ib Leunbach, Dragör, Denmark

[73] Assignee: Nycomed Innovation AB, Malmo, Sweden

[21] Appl. No.: 635,147

[22] PCT Filed: Jul. 25, 1989

[86] PCT No.: PCT/EP89/00875

§ 371 Date: Jan. 16, 1991

§ 102(e) Date: Jan. 16, 1991

[87] PCT Pub. No.: WO90/02343

PCT Pub. Date: Mar. 8, 1990

[30] Foreign Application Priority Data

Aug. 19, 1988 [GB] United Kingdom ............... 8819754

[51] Int. Cl.$^5$ ............................................. A61B 5/055
[52] U.S. Cl. ............................. 128/653.2; 128/653.4; 128/736; 324/315
[58] Field of Search ............... 128/653.2, 653.4, 736; 324/315

[56] References Cited

U.S. PATENT DOCUMENTS

| | | | |
|---|---|---|---|
| 3,502,964 | 3/1970 | Freeman | 324/315 |
| 4,284,949 | 8/1981 | Vidrine et al. | 324/315 |
| 4,558,279 | 12/1985 | Ackerman et al. | 324/315 |
| 4,914,608 | 4/1990 | LeBihan et al. | 324/315 |

Primary Examiner—Ruth S. Smith
Attorney, Agent, or Firm—Bacon & Thomas

[57] ABSTRACT

There is provided a method of and apparatus for thermographic imaging involving the use in electron spin resonance enhanced magnetic resonance imaging (ESREMRI) of a paramagnetic contrast agent having in its esr spectrum a temperature dependant transition. The ESREMRI enhancement of the free induction decay signal resultant on stimulating that transition with radiation of a set frequency or frequency band is itself accordingly temperature dependant.

18 Claims, 2 Drawing Sheets

THERMOGRAPHIC IMAGING

BACKGROUND OF THE INVENTION

The present invention relates to improvements in and relating to magnetic resonance imaging (MRI) apparatus and methods, and in particular to a method and apparatus for the thermographic imaging of a subject, generally although not essentially a human or animal body, and to contrast agents and media for use in such methods.

In certain cancer treatments, malignant tissue within the body is destroyed by irradiation with radiation, for example microwave radiation, which has sufficient heating effect to kill the malignant tissue, e.g. by raising the local temperature to about 43° C. As will readily be appreciated, the heating radiation can also kill healthy tissue and it is therefore of great importance for such treatments for the physician to be able to determine the temperature at and near the irradiated site.

This is particularly important since the radiation reflection and absorption characteristics are not uniform throughout the body and, especially where two or more directed radiation sources are used to achieve the heating effect, there is a danger that radiation reflection or shadowing by body tissue may cause areas of significant temperature increase ("hot-spots") to occur in healthy tissue or may prevent the temperature increase in part or all of the malignant tissue site from being sufficient to kill off all the malignant cells.

Several methods of temperature monitoring have been proposed, but to date all such methods have been either invasive, insufficiently accurate or time consuming or have enabled temperatures to be measured for superficial tissue layers only. Thus typical techniques which have been used include invasive monitoring by insertion of thermal sensing probes, infrared thermography, CAT scanning and NMR relaxation rate assessments.

There remains a need for a non-invasive thermographic imaging method capable of determining local temperatures throughout the body with reasonable accuracy.

We have now found that using a modification of our recently developed Electron Spin Resonance Enhanced Magnetic Resonance Imaging (ESREMRI) method thermographic imaging, or temperature monitoring, can be effected.

MRI is a diagnostic technique that has become particularly attractive to physicians as it does not involve exposing the patient to the harmful X-or gamma-radiations of conventional radiographic imaging techniques.

In our co-pending European Patent Application EP-A-296833 and British Patent Applications Nos. 8817137 and 8819753.8 we have described how the intensity of the magnetic resonance (MR) signal from which MR images are built up may be enhanced, e.g. by factors of 100 or more, by exciting an esr transition of a paramagnetic substance present within the subject being imaged where that esr transition is coupled to the nmr transition of the nuclei (generally protons and usually protons in water molecules) which emit the MR signals from which the MR images are built up.

The degeneracy of the spin states of nuclei with non-zero spin, e.g. $^1H$, $^{13}C$, $^{19}F$, etc., is lost when such nuclei are within a magnetic field and transitions between the ground and excited spin states can be excited by the application of radiation of the frequency ($\omega_o$) corresponding to energy difference E of the transition (i.e. $\hbar\omega_o = E$). This frequency is termed the Larmor frequency and is proportional to the strength of the applied field. As there is an energy difference between the spin states, when the spin system is at equilibrium the population distribution between ground and excited spin states is a Boltzmann distribution and there is a relative overpopulation of the ground state resulting in the spin system as a whole possessing a net magnetic moment in the field direction. This is referred to as a longitudinal magnetization. At equilibrium the components of the magnetic moments of the individual non-zero spin nuclei in the plane perpendicular to the field direction are randomized and the spin system as a whole has no net magnetic moment in this plane, i.e. it has no tranverse magnetization.

If the spin system is then exposed to a relatively low intensity oscillating magnetic field perpendicular to the main field and produced by radiation at the Larmor frequency, generally radiofrequency (RF) radiation in conventional MRI, transitions between ground and excited spin states occur. If the exposure is for a relatively short duration then the resultant magnitudes of the longitudinal and transverse magnetizations of the spin system are functions of the exposure duration which oscillate about zero at the Larmor frequency and are 90° out of phase with each other. Thus, from equilibrium, a pulse of duration $(2n+1)\pi/2\omega_o$ (a so-called 90° pulse when n is even and a 270° pulse when n is odd) leaves the system with maximum transverse magnetization (of magnitude proportional to the initial longitudinal magnetization at equilibrium) and no longitudinal magnetization, a pulse of duration $(2n+1)\pi/\omega_o$ (a 180° pulse) leaves the system with inverted longitudinal magnetization and inverted transverse magnetization (and hence from equilibrium no transverse magnetization), etc.

When the pulse is terminated, the oscillating magnetic field produced by any resulting net transverse magnetization can induce an oscillating electrical signal (of angular frequency $\omega_o$) in a detector coil having its axis arranged perpendicular to the main field direction. For this purpose the transmitter used to emit the pulse can also be used as a detector.

Induced nuclear magnetic resonance signals, hereinafter termed free induction decay (FID) signals, have an amplitude proportional to the transverse magnetization (and hence generally to the original population difference between ground and excited spin states).

If the nuclei of the spin system experienced an entirely uniform magnetic field, the FID signal would decay due to spin-spin interactions at a rate with a characteristic time of $T_2$, the transverse or spin-spin relaxation time. However, due to local field inhomogeneities, the nuclei within the spin system will have a spread of Larmor frequencies and decay of transverse magnetization is more rapid, having a characteristic time of $T_2^*$ where $1/T_2^* = 1/T_2 + 1/T_{inh}$, $T_{inh}$ representing the contribution due to field inhomogeneities. $T_2$ itself can be determined using spin-echo imaging in which, after the decay of the FID signal (usually following a 90° pulse) the system is exposed to a 180° pulse and an "echo" signal is generated, the decay in the amplitude of the echo being governed primarily by $T_2$ as, with the inversion of the transverse magnetization for the individual nuclei, the field inhomogeneities referred to above cause tranverse magnetization to build up to a maximum at time TE/2 after the 180° pulse where the time between the previous maximum transverse magnetization and the 180° pulse is also TE/2.

To generate different images, different pulse and FID detection sequences are used. Perhaps the simplest is saturation recovery (SR) where the FID signal is determined after a single 90° initiating pulse. The signal strength is dependent upon the magnitude of the longitudinal magnetization before the pulse, and hence on the nuclear density and the extent to which the system reequilibrates in the time (TR) between successive initiating pulses. In spin-echo imaging, for example multiple-echo imaging, the pulse and detection sequence may be: initiating 90° pulse (at time 0), FID detection (following the initiating pulse), 180° pulse (at time TE/2), detection of 1st echo (at time TE), 180° pulse (at time 3TE/2), detection of 2nd echo (at time 2TE) . . . , initiating pulse for the next sequence (at time TR), etc. In this technique, a TR is selected which is sufficient for a reasonable reequilibration to occur in the period between successive initiating pulses.

As is explained further below in connection with the example of two dimensional Fourier transformation (2DFT) image generation, in order to generate a single image with adequate spatial resolution, it is necessary to perform a large number (e.g. 64-1024) of separate pulse and detection sequences.

Since TR has in principle to be large with respect to $T_1$, the characteristic time for relaxation of the excited system towards the equilibrium Boltzmann distribution between ground and excited spin states, to permit longitudinal magnetization to build up between successive pulse sequences so as to avoid the FID signal strength decaying in successive pulse sequences, the total image acquistion time is generally relatively large. Thus, for example, TR may conventionally be of the order of seconds and the image acquisition time may be of the order of 10-30 minutes.

Certain so-called fast imaging (FI) techniques may be used to accelerate reequilibration and so reduce image acquisition time; however they inherently result in a reduction in the S/N ratio and/or contrast hence in poorer image quality. The FI technique involves for example exciting the spin system with a less than 90° pulse and thus the difference between ground and excited spin state populations is only reduced rather than eliminated (as with a 90° pulse) or inverted and so reattainment of equilibrium is more rapid. Nevertheless, the transverse magnetization generated by the less than 90° pulse is less than that for a 90° pulse and so FID signal strength and thus S/N ratio and the spatial resolution in the final image are reduced.

Using different pulse and detection sequences and by manipulation of the acquired data, MRI can be used to generate a variety of different images, for example saturation recovery (SR), inversion recovery (IR), spin echo (SE), nuclear (usually proton) density, longitudinal relaxation time ($T_1$) and transverse relaxation time ($T_2$) images. Tissues or tissue abnormalities that have poor contrast in one such image often have improved contrast in another. Alternatively, imaging parameters (nuclear density, $T_1$ and $T_2$) for tissues of interest may be altered by administration of a contrast agent. Thus many proposals have been made for the administration of magnetically responsive materials to patients under study (see for example EP-A-71564 (Schering), U.S. Pat. No. 4,615,879 (Runge), WO-A-85/02772 (Schröder) and WO-A-85/04330 (Jacobsen)). Where such materials, generally referred to as MRI contrast agents, are paramagnetic (for example gadolinium oxalate as suggested by Runge) they produce a significant reduction in the $T_1$ of the water protons in the zones into which they are administered or at which they congregate, and where the materials are ferromagnetic or superparamagnetic (e.g. as suggested by Schröder and Jacobsen) they produce a significant reduction in the $T_2$ of the water protons, in either case resulting in enhanced (positive or negative) contrast in the magnetic resonance (MR) images of such zones.

The contrast enhancement achievable by such agents is limited by a number of factors. Thus such contrast agents cannot move the MRI signal intensity ($I_s$) for any tissue beyond the maximum ($I_l$) and minimum ($I_o$) intensities achievable for that tissue using the same imaging technique (e.g. IR, SR, SE, etc.) in the absence of the contrast agent: thus if "contrast effect" is defined as $(I_s-I_o)/(I_l-I_o)$, contrast agents can serve to alter the "contrast effect" of a tissue within the range of 0-1. However to achieve contrast improvement an adequate quantity of the contrast agent must be administered to the subject, either directly to the body site of interest or in such a way that the natural operation of the body will bring the contrast agent to that body site.

ESREMRI utilises the spin transition coupling phenomenon known in conventional nmr spectroscopy as the Overhauser effect to amplify the population difference between ground and excited nuclear spin states, producing a significant overpopulation (relative to the Boltzmann distribution population) of the excited spin state of the nuclear spin system producing the MR image. This is achieved by exciting a coupled esr transition in a paramagnetic species naturally occurring in or introduced into the sample being imaged, which is generally but not essentially a human or animal subject.

The MRI apparatus for use according to this technique requires a second radiation source for generating the radiation capable of stimulating such an esr transition as well as the first radiation source for generating the radiation used to stimulate the nuclear spin transition.

SUMMARY OF THE INVENTION

The present invention is based on the fact that many paramagnetic species have esr spectra in which one or more of the peaks is temperature dependent. By carrying out the ESREMRI technique using a constant MW source at the central frequency of the temperature dependent peak at a reference temperature, e.g. ambient temperature, the shift caused by increased temperature will move the peak relative to the MW frequency and thus alter the resonance induced; this in turn alters the esr enhancement of the FID signal and the extent of this alteration can be used to estimate the temperature difference from the reference temperature.

In general, the esr spectrum will consist of peaks of significant line width and will thus lie between limiting frequencies on either side of the central frequency. The shape of the peak is thus such that there is a continuous and well defined fall in signal strength on moving away from the central frequency. Provided the frequency shift due to changing temperature is not so great that MW frequency falls outside the limiting frequencies of the peak after the temperature change, the signal strength on stimulation with constant MW frequency as described above will alter in a relatively continuous and calculable way as the temperature changes. If the frequency shift is so large as not to fulfil this requirement, then it is possible to repeat the ESREMRI measurement using a constant MW frequency corresponding to a reference temperature closer to the temperature to be measured.

Viewed from one aspect the present invention provides a method of determining temperature of at least one site of a body containing a paramagnetic substance having a first esr transition the central frequency of which is temperature dependent, said method comprising exposing said body to a first radiation of a frequency selected to excite nuclear spin transitions in selected nuclei in said body, exposing said body to a second radiation of a frequency selected to excite said esr transition, said second radiation being at the central frequency of the said esr transition at a selected reference temperature, detecting free induction decay signals from the body, and from the said free induction decay signals generating a signal indicative of the temperature at said site and, optionally, generating an image indicative of temperature distribution in said body.

DETAILED DESCRIPTION OF THE INVENTION

Figure 1:
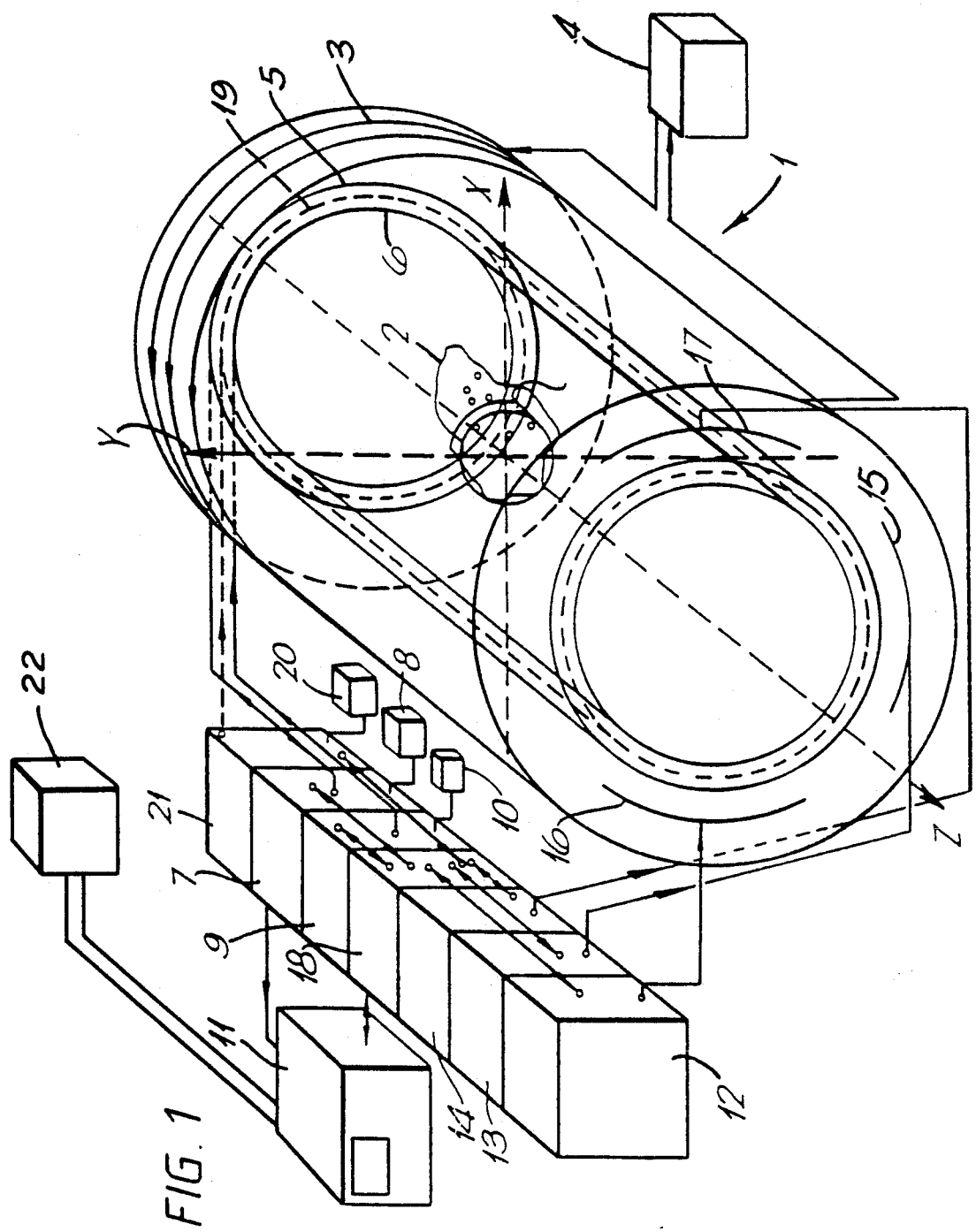

In the methods of the invention exposure of the body to the RF radiation will generally be in a series of pulse sequences with exposure to MW radiation occurring during at least one and generally a plurality of such sequences.

It will be appreciated that the reference temperature may be different from ambient temperature, conveniently above ambient where elevated temperatures are to be measured. Thus in effect, the MW frequency of the second radiation may be any frequency corresponding to a temperature close enough to the unknown temperature to ensure that the frequency still falls within the frequency limits of the temperature-shifted esr peak at some part of the temperature range of interest.

For temperature measurement at one or more sites within the body being examined (voxels) it will be necessary to use the techniques of MRI and for this there will thus be at least a magnetic field gradient to provide the necessary slicing and normally phase encoding and read gradients will be applied at the appropriate times. In this way, either individual voxels within the body can be examined or a complete topographic thermal image of the body can be built up.

In general, the free induction decay (FID) signals from any particular volume (voxel) within the said body will depend on a number of parameters each of which may vary widely, so that the magnitude of the FID signals alone will in most cases give only an inaccurate estimation of temperature. Consequently, it is in general desirable to employ means whereby the effect of the variable paramaters can be eliminated.

One parameter of importance is the concentration of the paramagnetic species in the voxel concerned. In human tissue, relative uptakes of the paramagnetic species are not at all uniform even in a single tissue. Thus, a low FID signal could be due to low concentration of the paramagnetic species at the voxel concerned and if the concentration is unknown and/or variable, it will be difficult to derive the temperature change from the FID information.

The MW power that is the power of the esr exciting radiation, at any particular voxel will be generally lower than the applied MW power due to absorption by intervening tissue and other factors. Again, a reduction in local MW power gives a lower FID signal and will be relevant to the temperature determination.

Other variable parameters are $T_1$ and $T_2$ of the esr transition ($T_{1e}$ and $T_{2e}$).

The equations and explanations for signal enhancement variations are offered by way of illustration and the efficacy and utility of the invention is in no way dependent on their accuracy. Thus the enhancement caused by esr transition stimulation and the FID signal strength can for large enhancements and short repetition times be represented by Equation 1:

$$E = \tfrac{1}{2}K_1(1-(1+F(P_v,WL,\Delta t)+WL.Y^2.P_v)^{-1})(1-e^{K_2 c})$$

where
  E represents the signal enhancement;
  $\Delta t$ is the difference between the temperature of the voxel and the reference temperature;
  WL is the product of $T_{1e}$ and $T_{2e}$ where $T_{1e}$ is $T_1$ for the esr transition and $T_{2e}$ is $T_2$ for the esr transition;
  $K_1$ is the gyromagnetic ratio of the electron to the proton
  Y is the gyromagnetic constant of the electron;
  $P_v$ is the MW power within the voxel;
  C is the concentration of the paramagnetic substance within the voxel;
  $K_2$ is a constant; and
  $F(P_v, WL, \Delta t)$ is a function related to the change from saturation or maximum resonance due to the temperature change, being zero where there is no temperature dependent change. This function is dependent on $\Delta t$ in the sense that the shift in the position of the central frequency of the temperature dependent esr peak is proportional to $\Delta t$.

Since enhancement of the FID signal can be up to 100 or even 200 times, the enhancement will be the predominant factor in determining FID signal strength and consequently as an approximation, the signal strength S can be represented as KE where K is a constant. In general, therefore, the effect of the nature of the RF pulse sequence and of the possible effect of sub-volumes of zero concentration of contrast agent in the volume or voxel to be investigated can be excluded, particularly when ratios of FID signal strengths are concerned as in the calculations discussed below.

If it were possible to keep all the variable parameters constant, then measurement of the reduced FID signal would be capable of providing the temperature change directly, either by calculation or calibration. In practice, this is extremely difficult, and according to a further preferred aspect of the invention; we reduce this problem by selecting a paramagnetic substance which has at least two esr transitions, one of which is invariant with temperature and one of which is temperature dependent.

We have found that certain nitroxide free radicals used as paramagnetic contrast agents in ESREMRI, in particular 4-oxo-2,2,6,6-tetramethyl piperidine-1-oxyl, have an esr spectrum comprising a triplet the central peak of which is temperature invariant and the side peaks of which are temperature dependent.

According to this important embodiment of the invention, in addition to the radiation exciting the temperature dependent esr transition, and that exciting nuclear spin transitions, the body is also exposed to a third radiation exciting a second esr transition, the central frequency of which is substantially temperature independent. Conveniently in this embodiment the body is exposed to a series of pulse sequences of the first radiation and is exposed to the second radiation during a first set of the sequences and to the third radiation during a second set of the sequences. The signal or image indicative of temperature can then be generated from the FID signals detected in the first and second sets, e.g. pluralities, of pulse sequences.

In this case, the second esr transition will be at resonance throughout and the function $F(P_v.WL.\Delta t)$ in the above equation will be zero. Furthermore many of the parameters in Equation 1, in particular local concentration of the paramagnetic contrast agent, will be the same in respect of both transitions and consequently, the ratio of the FID signals, being approximately proportional to the respective signal enhancements, will exclude many of the common terms by cancelling out.

Since Y is a constant, under the above circumstances, the only other variable parameter in Equation (1) is $P_v$, the local MW power at the voxel. If the relative strengths of the FID signals for the two transitions are determined again at a different applied MW power level, it is possible to eliminate $P_v$ on the experimentally verified assumption that $P_v$ is a constant fraction of the applied power. $P_v$ can thus be replaced in the above equation by A.P, where P is the applied MW power and A is a constant for the voxel concerned related to the transmission (i.e. non-absorption) of the MW radiation at that site.

It should be noted that since the two esr peaks are part of a multiplet, usually a triplet, the esr relaxation time $T_{1e}$ is the same for both peaks, as is $T_{2e}$ and WL will thus be substantially the same for both peaks and for any particular voxel will be the same in each of the equations for the FID signal strength as set out below.

One can thus derive equations as follows:

Temperature Invariant Peak A $$SR_{1,2}^A = \frac{S_1^A}{S_2^A} = \frac{E_1^A}{E_2^A} = \frac{P_1}{P_2} \cdot \frac{1 + (Y^2 \cdot WL \cdot A \cdot P_2)}{1 + (Y \cdot WL \cdot A \cdot P_1)}$$

(where $S_1^A$ and $E_1^A$ are the FID signal stengths and enhancement factor E for peak A at power level 1 and $SR_{1,2}^A$ ratio of FID signal strengths $S_1^A$ and $S_2^A$) because $F(AP,\Delta t,WL)$ is zero when there is no change from resonance with temperature (i.e. when $\Delta t$ is zero), and WL is substantially the same for both power settings. This enables the product ($Y^2$, WL A) to be determined knowing $P_1$ and $P_2$ and thus the value of A.WL.

Temperature Variable Peak, B $$SR_{1,2}^B = \frac{S_1^B}{S_2^B} = \frac{E_1^B}{E_2^B} = \frac{1 + F(AP_1,\Delta t,WL) + Y^2 \cdot WL \cdot A \cdot P_2)}{1 + F(AP_2,\Delta t,WL) + Y^2 \cdot WL \cdot A \cdot P_1)} \quad \frac{F(AP_1,\Delta t,WL) + Y^2 \cdot WL \cdot A \cdot P_1)}{F(AP_2,\Delta t,WL) + Y^2 \cdot WL \cdot A \cdot P_1)}$$

Since A.WL has been determined and $P_1$ and $P_2$ are known, the latter equation can be solved for $F(AP,WL,\Delta t)$. It will be noted that since the term $(1 - e^{K2c})$ in Equation (1) remains the same throughout, it cancels out when ratios of FID signal strengths are determined.

The nature of the function $F(AP.WL.\Delta t)$, which is related to the shape of the esr peak, can be determined by preliminary calculation and calibration for different levels of power, WL and temperature. From such calibration, it is possible to readily derive $\Delta t$ from the value for $F(AP_1.WL,\Delta t)$. It should be noted that although WL and A may vary from voxel to voxel, partly due to concentration effects, the above calculation will be made independently for each voxel and it is only necessary that WL and A are the same throughout the equations for the particular voxel concerned.

However, the sign of the function $F(AP,\Delta t,WL)$ will be the same for both upward and downward temperature changes, because the substantially symmetrical shape of the esr peak means that departures from resonance or saturation will be caused by both upward and downward temperature changes, it may be necessary to establish whether $\Delta t$ has a +ve or −ve sign. Where it is possible to establish a definite increase in temperature by other means, this may not be necessary but in general, a further step is required to determine the sign of $\Delta t$.

This can, however, readily be achieved by a further determination of the FID signal strength using an MW frequency close to but different from the MW frequency providing resonance at the reference temperature, for example an MW frequency corresponding to resonance at a temperature slightly above the reference temperature. The method of the invention will then involve exposing the body to a fourth radiation of a frequency selected to excite the first esr transition the fourth radiation being at the central frequency of said first esr transition at a second selected reference temperature. If $\Delta t$ is positive, that is the temperature has increased, the esr transition will be closer to resonance which will increase the signal enhancement factor E and thus the FID signal thereby indicating the positive sign of $\Delta t$.

In fact, this further measurement can, under some circumstances, taken together with the FID signal at the original MW frequency for the temperature dependent peak, provide sufficient information to enable t to be determined without reference to the temperature invariant peak.

Thus, the most preferred procedure according to the invention for measuring temperature at a site in a body, for example a human body, is as follows:

1. Cause a paramagnetic MRI contrast agent of the appropriate kind to be distributed throughout the body.

2. Expose the body under magnetic field conditions for generating FID signals at that said site to a series of pulse sequences of the first radiation exciting nuclear spin transition (normally proton spin transitions since, in the case of the human body, water molecules are adequately widely distributed).

3. Expose the body within a first plurality of the pulse sequences of (2) to a second radiation being at the central frequency of a temperature dependent esr transition of the contrast agent, said frequency being that causing maximum resonance at a reference temperature and being at a constant, known power level.

4. Measuring the FID signals so generated.

5. Expose the body within a second plurality of the pulse sequences of (2) under the same magnetic field conditions (and thus relating to essentially the same voxel) at the, central frequency of a temperature independent esr transition of the paramagnetic substance and being at the same power level as (3).

6. Measuring the FID signals from the body generated by (5).

7. Repeating (2) to (6) under the same magnetic field conditions at different power level of the two esr exciting frequencies.

8. Repeating (3) and (4) under the same magnetic field conditions at a slightly different frequency in order to determine the sign of the temperature deviation from the reference temperature, $\Delta t$.

9. By a suitable algorithm, solving the foregoing equations to give a value of $\Delta t$ in a particular voxel of the body.

10. If desired, repeating steps (1)–(9) at different magnetic field settings to determine $\Delta t$ in different voxels of the body, for example, producing a thermal tomographic image of the body.

Thus the method of the invention preferably involves the following steps:

a) distributing a said paramagnetic substance within said body;
b) exposing said body to a series of pulse sequences of said first radiation;
c) exposing said body during a first set of said sequences to said second radiation at a first selected power level;
d) detecting free induction decay signals from said body in said first set of sequences;
e) exposing said body during a second set of said sequences to said third radiation at said first selected power level;
f) detecting free induction decay signals from said body in said second set of sequences;
g) exposing said body during a third set of said sequences to said second radiation at a second selected power level;
h) detecting free induction decay signals from said body in said third set of sequences;
i) exposing said body during a fourth set of said sequences to said third radiation at said second selected power level;
j) detecting free induction decay signals from said body in said fourth set of sequences;
k) exposing said body during a fifth set of said sequences to said fourth radiation at said first selected power level;
l) detecting free induction decay signals from said body in said fifth set of sequences; and
m) generating from the free induction signals detected in steps (d), (f), (h), (j) and (l) a said signal or image indicative of temperature.

It will be appreciated that the applied MW power should be selected to ensure that the signal enhancement is adequately temperature dependent. Furthermore, the MW power should not be such that undue heating of the body takes place. Such heating can be reduced by selecting esr transitions in which $T_{1e}$ and $T_{2e}$ are both long; the nitroxide free radical contrast agents are satisfactory in this respect.

For the performance of the method of the invention there may be used an ESREMRI apparatus provided with a nuclear magnetic resonance transition stimulating radiation source and a source or sources for at least one, preferably two or more, esr transition stimulating radiation, and preferably provided with means for adjusting power levels of at least the latter source(s). Such an apparatus having means for sequentially stimulating multiple esr transitions, is new and constitutes a further feature of the invention.

Thus viewed from a further aspect the invention provides a temperature determining apparatus, preferably a magnetic resonance imaging apparatus, comprising a first radiation source capable of emitting pulse sequences of a first radiation of a frequency selected to excite nuclear spin transitions in a body, means for detecting free induction decay signals from said selected nuclei, a second, third and optionally and preferably at least a fourth radiation source arranged respectively to emit during selected said pulse sequences second, third and optionally and preferably fourth radiations of selected frequencies capable of exciting in a paramagnetic substance present in said body one or optionally and preferably at least two electron spin transitions coupled to the nuclear spin transitions of at least some of said nuclei (said second, third and where present fourth and further radiation sources preferably being provided with control means arranged to permit selection of the timing, power and frequency of the second and higher radiations), and generating means arranged to generate a signal indicative of the temperature at one or more sites of said body (preferably an image indicative of the temperature distribution in said body) from the free induction decay signals detected by said means for detecting during pulse sequences in which said body is exposed to said second or third or where appropriate said fourth and higher radiations.

The apparatus of the invention can if desired be provided with a primary magnet means capable of generating a uniform magnetic field, e.g. of conventional or lower than conventional field strength, for example 0.01 to 2T. However magnet construction and operation are a major factor in the high cost of conventional MRI apparatus and since the contrast effect achievable with ESREMRI is so high the apparatus of the invention may if desired be provided with a very low field strength primary magnet, e.g. a magnet capable of generating a field of from 0 to 0.01 T, e.g. about 15 G (1.5 mT), or even with no magnet whatsoever. In the latter case, the uniform magnetic field in the MRI procedure is provided by the earth's ambient field. There will however normally be means for generating the magnetic field gradients which enable the FID signals from particular sites in the body, preferably the complete array of voxels forming a complete image of the body, to be distinguished. ESREMRI apparatus without primary magnets, and contrast agents for use therewith, are disclosed in our copending British Patent Application No. 8819753.8.

Operating at the primary magnetic fields of conventional MRI, the radiation required to stimulate nuclear spin transitions, the first radiation, is generally radiofrequency (RF) radiation, and the radiation required to stimulate esr transitions, the second and higher radiations, is generally microwave (MW) radiation. At lower fields or at ambient field radiations of lower frequencies are required but for the sake of easy comprehension the first radiation and the first radiation source will be referred to hereinafter as "RF" radiation and an "RF" source and the second and higher radiations and the second and higher radiation sources will be referred to as "MW" radiations and "MW" sources It must be borne in mind however that, especially where very low field primary magnets or no primary magnets are used, the "MW" and "RF" radiations may be at frequencies not normally considered to be MW or RF.

The first radiation source is preferably provided with means for adjusting the pulse timing and duration so that the desired imaging technique (e.g. SR, IR, SE, FI, etc.) may be chosen and so that the pulse sequence repetition rate 1/TR may be selected to increase or reduce image acquisition time or to determine $T_1$, $T_2$ or nuclear (usually proton) density.

The first radiation source is also preferably provided with means for adjusting the central frequency, bandwidth, and intensity of the first radiation pulses.

In MRI, the radiation pulse which excites the resonating nuclei is applied while the sample is in a magnetic field conventionally with a field gradient in one direction (e.g. the Z direction). The central frequency and bandwidth of the nuclei exciting pulse, together with the Z direction field gradient during the exciting pulse, serve to define the position along the Z axis and the thickness in the Z direction of the slice perpendicular to the Z axis containing nuclei whose spin transitions are excited by that pulse. Thus, for example, Fourier transformation of a square wave pulse of central frequency $V_0$ would show such a pulse to contain a range of frequencies centered about $V_0$ and each corresponding to the Larmor frequency of resonating nuclei in a particular XY plane along the Z axis. Thus by providing the apparatus with means for adjusting or selecting the central frequency and bandwidth of the first radiation, the section through the body (the image zone), and of course the isotopic nature and chemical environment of the resonating nuclei, may be selected.

The second and higher radiation sources may be one or several emitters which may be continuous wave (CW) transmitters or may be arranged to emit pulses or trains of pulses of the second and higher radiations.

To achieve the full benefit of the amplified FID signal of the nuclear spin system and to minimise the required dosage of the paramagnetic substance, it is therefore beneficial to use second and higher radiation sources capable of emitting a band of frequencies (e.g. in pulse trains) or to use as the sources of each of the second and higher radiations two or more sources emitting at different frequencies. Insofar as the third radiation is concerned it is clearly desirable to excite the second esr transition as far as is practicable; for the second, fourth and higher radiations however the method of the invention requires that the degree of saturation of the first esr transition should vary with temperature and the bandwidths or sets of frequencies of the second, fourth and higher radiations should be selected accordingly.

To achieve the desired frequency spread in the second and higher radiations, it may be desirable to use pulses of relatively short duration (hereinafter "micropulses"), for example of the order of nano or microseconds, and to optimize the amplified population difference of the nuclear spin system it may thus be desirable to arrange the second and higher radiations source to emit a train of micropulses, the adjacent micropulses being so spaced as not to permit serious longitudinal relaxation of the electron spin system in the periods between the micropulses.

The apparatus may also if desired be provided with a decoupling means comprising a further radiation source arranged to emit radiation capable of exciting spin transitions in certain nuclei (other than the resonating nuclei, that is those nuclei that are responsible for the MR signals from which the temperature indicative signal or image is generated) in order to reduce the number of peaks or peak widths in the esr spectrum of the paramagnetic substance. Where such decoupling means are provided they should be used only if the resulting partially decoupled esr spectrum still contains the temperature independent and temperature dependent second and first transitions required for performance of the method of the invention. The further radiation emission may be continuous or pulsed (or may take form of a continuous train or a series of trains of micropulses as described earlier for the second radiation) and suitably is emitted over substantially the same periods as the second and higher radiations.

The second and higher radiation source(s) and, where present, the further radiation source will therefore, like the first radiation source, preferably be provided with means for adjusting pulse timing, pulse duration, central frequency, bandwidth and intensity if they are pulsed sources, and central frequency, bandwidth and intensity if they are CW emitters.

In the method of the invention the sample is preferably exposed to one of the second and higher radiations for at least part of each pulse sequence, i.e. during at least part of the period between the initial pulses of adjacent said sequences. Preferably exposure to the second and higher radiations will be for some, the major part or all of the period during which no magnetic field gradient is imposed on the sample. Conveniently therefore one of the second and higher radiations may be applied following FID signal determination in each pulse sequence, i.e. in the decay period.

It will be appreciated that for certain imaging techniques, particularly saturation recovery (SR) each "pulse sequence" may only involve one pulse of the first radiation while in other MR imaging techniques each pulse sequence may involve several pulses of the first radiation.

A magnetic resonance image of the sample can be generated from the detected FID signals in the conventional manner and the generation of the temperature indicative signal or image can be effected for example by manipulation of the raw FID signals or by manipulation of the processed signals, e.g. data corresponding to the MR images for the first, second and higher pluralities of pulse sequences. Thus generally the apparatus of the invention will comprise means, generally a computer, for generating the temperature indicative signals or images and generally also for transforming sets of detected FID signals, before or after manipulation to extract temperature information, into images.

The apparatus of the invention should particularly preferably be arranged to operate as a conventional ESREMRI or MRI apparatus and so the control means should be arranged to permit the apparatus if desired to be operated with only the first and second radiations or only the first radiation respectively. Similarly if the apparatus is operable without a primary magnet it may nonetheless be preferable to provide the apparatus with a primary magnet energisable on operation of selection means so that the apparatus can function for thermographic imaging, for ESREMRI or for conventional MRI at higher fields. The apparatus is preferably arranged to permit MRI or ESREMRI of the body and in certain instances may simply constitute a conventional MRI or ESREMRI apparatus provided with the extra radiation sources and data handling means mentioned above. The image generation procedure involved in the use of the apparatus and the method of the invention may also involve any one of the conventional image generation procedures, such as for example back projection or three- or two-dimensional Fourier transformation (3DFT and 2DFT), although the latter two of these may generally be preferred.

In 2DFT, the sample is placed in a magnetic field (the field direction being the Z direction) and is allowed to equilibrate. A small field gradient (the slice selection gradient) is then applied, e.g. in the Z direction, and while the slice selection gradient is superimposed on the main field the sample is exposed to an RF pulse (the initiating pulse) of a given central frequency, bandwidth and duration. Together, the central frequency, the bandwidth and the combination of the main field and the slice selection gradient serve to define the position and thickness of the image zone, the tomographic section through the sample transverse to the slice selection gradient in which the resonating nuclei will be excited by the RF pulse. The duration of the pulse determines the resultant change in transverse and longitudinal magnetization of the resonating nuclei. With a 90° pulse, after the slice selection gradient and the RF pulse are simultaneously terminated, a small field gradient (the phase encoding gradient) is then imposed for a short period in a direction transverse to the slice selection gradient, e.g. in the Y direction, causing the phase of the oscillating FID signal to become dependant on the position in the Y direction of the signal's source and thus encoding spatial information in the phase of the FID signal. After the phase encoding gradient is terminated, a third small field gradient the read gradient) in a direction perpendicular to the previous two (the X direction) is imposed to encode spatial information in the FID frequency and the FID signal is detected and its intensity as a function of time is recorded during the imposition of the read gradient.

The FID signal that is detected is the combination of signals from resonating nuclei throughout the image zone. If in simple terms it is viewed as the sum of signals from an array of sources extending in the XY plane, the oscillating signal from each source will have an overall intensity dependent on the local density of the resonating nuclei, a frequency dependant on the position of the source in the X direction and a phase dependant on the position of the source in the Y direction.

The read gradient is terminated after the FID signal decays and, after a delay time to permit equilibration, the slice selection gradient is reimposed and the initiating RF pulse of the subsequent pulse sequence is applied.

Image generation requires detections of the FID signal for a series of pulse sequences, each with a phase encoding gradient of different strength or duration, and two-dimensional Fourier transformation of the resultant data can extract the spatial information to construct a two dimensional image, in the case described an SR image.

Different imaging techniques, such as IR, SE, etc., or different image generation techniques, e.g. simultaneous slice, volume acquisition, back projection etc., will of course require different pulse and field gradient imposition sequences, sequences which are conventional in the art.

The paramagnetic substance possessing the esr transitions which are excited by the second and higher radiations may be naturally present within the body being thermographically imaged or, more usually, may be introduced thereinto as a contrast agent. Coupling with the resonating nuclei may be either scalar coupling with resonating nuclei within the same molecules as the unpaired electrons or dipolar coupling with resonating nuclei, generally water protons in the body fluids, in molecules in the environment of the paramagnetic centres.

Electron spin systems do occur naturally in the body, e.g. in substances synthesized in certain metabolic pathways such as the oxidation chain in the cell mitochondria, although normally at low concentration.

Insofar as administered contrast agents are concerned however, in one embodiment of the invention there may be used a contrast medium which contains both the resonating nuclei and the substance possessing the desired electron spin transition, and in a further embodiment the substance possessing the desired electron spin transition may itself also contain one or more of the resonating nuclei. This is especially preferred where the resonating nuclei are rarely abundant in the sample being imaged, for example where the resonating nuclei are $^{13}C$ or $^{19}F$ nuclei where scalar coupling will be important in the amplified FID.

Alternatively, and generally more preferably, the contrast agent may contain a paramagnetic centre which undergoes dipolar coupling with resonating nuclei naturally occurring in the sample, e.g. in body tissue, or more specifically with resonating protons in water molecules in the sample.

In the method of the invention, selection of the esr system which couples with the resonating nuclei is particularly important where the method is to be performed on a live subject. Where the body is living it is generally preferable that exposure to penetrating or heating radiation be minimised and thus it is desirable to select a paramagnetic substance for which the electron relaxation times $T_{2e}$ and $T_{1e}$ are relatively long under the local concentration and magnetic field conditions and also if possible to use a low primary field so that the required "MW" radiation has minimal heating effect.

The linewidths of esr transitions (i.e. full widths at half maximum in the absorption spectrum) are dependent on concentration and magnetic field and the paramagnetic contrast agent will preferably have, at the imaging conditions, an esr spectrum wherein the temperature dependent peak has a width sufficiently large as to permit an esr enhanced FID signal to be detected over the full temperature range of interest, e.g. 36° to 45° C. for hyperthermia treatment. In general, the esr peak widths will preferably be from about 50 milliGauss to 2 Gauss (5 $\mu$T to 0.2 mT), especially preferably 100 to 1500 milliGauss (10 to 150 $\mu$T), more particularly 150 to 800 milliGauss (15 to 80 $\mu$T) (or the frequency equivalents). Thus conventional paramagnetic MRI contrast agents such as the gadolinium compounds (e.g. Gd DTPA) suggested by Schering AG in EP-A 71564 would not generally be selected.

The esr spectrum of the paramagnetic substance, as mentioned above, must contain a temperature dependent peak and preferably a temperature independent peak. If the spectrum contains further peaks it is generally preferred that the total number be small, e.g. 2–10, especially preferably 3–5, and that the separation of the temperature dependent transition from the temperature independent transition should be as large as possible, e.g. greater than 2 Gauss (0.2 mT), preferably greater than 10 Gauss (1 mT), especially preferably greater than 15 Gauss (1.5 mT) (or the frequency equivalent thereof), especially at ambient magnetic field or low primary magnetic fields.

Although it is preferred that the temperature dependent and invariant esr peaks of the paramagnetic substance are those of a doublet or triplet it is generally preferable to reduce hyperfine splitting in the esr spectrum, and thereby keep the number of peaks in the spectrum small. Consequently, the paramagnetic substance will preferably be a molecule containing few non-zero spin nuclei or few non-zero spin nuclei in the vicinity of the paramagnetic centre (e.g. the oxygen of a nitroxyl NO moiety). Conveniently, the molecule may have the atoms near to the paramagnetic centre predominantly selected from zero nuclear spin isotopes or from elements for which the natural abundance of non-zero spin nuclear isotopes is low. Such selection may include elements in which the natural abundance of spin $=\frac{1}{2}$, nuclei is low and isotopes such as $^{12}C$, $^{2}H$, $^{32}S$, $^{14}Si$ and $^{16}O$ may for example be used to build up the molecular structure adjacent, to the location of the unpaired electron.

Particularly interesting as paramagnetic substances for use in the present invention are the stable free radicals and in particular the nitroxide stable free radicals many of which have been suggested in the literature for use as spin labels or as paramagnetic contrast agents for conventional MRI. Moreover, several of these compounds are readily available commercially, for example from Aldrich. The nitroxide stable free radicals are of particular interest as their toxicities and pharmacokinetics have been studied and show the compounds to be suitable for in vivo MRI. A further particularly interesting group of stable free radicals are the deuterated nitroxide stable free radicals of which several have also been suggested in the literature for use as spin labels.

Where the stable free radicals are only partially deuterated, it is especially preferred that the hydrogens at those sites where $^{1}H$ would cause the greatest, or indeed any significant, reduction in the $T_{1e}$ or $T_{2e}$ values for the unpaired electron should be $^{2}H$.

Deuterated radicals used according to the invention preferably have deuterium atoms in place of protons within 3, preferably 4 and especially preferably 5 or more, bonds of the paramagnetic centre, e.g. the oxygen of an NO moiety. More especially the radicals are preferably perdeuterated; however where radicals contain labile hydrogens, e.g. acid, amine or alcohol hydrogens, these may preferably be $^{1}H$ and compounds containing hydrogens distant from the paramagnetic centre which are $^{1}H$ may also be used to advantage.

As nitroxide stable free radicals, or deuterated nitroxide stable free radicals, there may conveniently be used cyclic nitroxides wherein the NO moiety occurs in a 5 to 7-membered saturated or ethylenically unsaturated ring with the ring positions adjacent to it being occupied by doubly saturated carbon atoms and with one of the remaining ring positions being occupied by a carbon, oxygen or sulphur atom and the remaining ring positions being occupied by carbon atoms. Alternatively there may be used as the optionally deuterated nitroxide stable free radicals compounds in which the NO moiety occurs in a chain where the adjacent chain atoms are carbon and are not bound to any protons.

Preferred nitroxides may be represented by the formula (I)

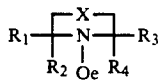

(I)

wherein $R_1$ to $R_4$ may represent deuterium or lower (for example $C_{1-4}$) alkyl or hydroxyalkyl groups and $R_1$ may also represent carboxy substituted $C_{1-10}$ alkyl groups and $R_2$ may also represent a higher (e.g. $C_{5-20}$) alkyl group or a carboxy substituted $C_{1-20}$ alkyl group, or $R_1$ and $R_3$ may together represent an alkylene or alkenylene group, e.g. having up to 4, especially preferably up to 3, carbon atoms and X represents an optionally substituted, saturated or ethylenically unsaturated bridging group having 2 to 4 atoms in the backbone of the bridge one of the backbone atoms being carbon, oxygen or sulphur and the remaining backbone atoms being carbon, preferably with one or more of $R_1$ to $R_4$ and X comprising at least one deuterium, especially preferably any carbon-bound hydrogen within three, and especially preferably within 4, bonds of the nitroxyl nitrogen being a deuterium atom.

In formula I, the molecule is preferably assymetric and the moieties $CR_1R_2$ and $CR_3R_4$ are preferably different but $R_1$ to $R_4$ are nonetheless preferably deuterium atoms or deuterated alkyl groups.

In formula I the optional substitution on X, which preferably is an optionally mono-unsaturated $C_{2-3}$ chain, may for example take the form of halogen atoms or oxo, amino, carboxyl, hydroxy or alkyl groups or combinations or derivatives thereof such as for example amide, ester, ether or N-attached heterocyclic, e.g. 2,5-dioxopyrrolidino, groups. Many examples of substituted X groups are described in the literature mentioned in our copending applications.

The nitroxide molecule may if desired be bound to a further substance, such as for example a sugar, polysaccharide, protein or lipid or to other biomolecules, for example to enhance the blood pooling effect or the tissue- or organ-targetting ability of the nitroxide stable free radical.

In the method and use of the invention there may particularly conveniently be used nitroxide stable free radicals selected from those described in our copending patent applications mentioned above.

A further selection criteria for the paramagnetic substance use in the method of the invention is that, where the body on which the method is performed is cellular, e.g. a human or non-human animal, the substance should preferably distribute predominantly in the extracellular space.

In a still further aspect the invention thus provides the use of a physiologically tolerable paramagnetic material having a temperature dependent and preferably also a temperature independent transition in its esr spectrum, e.g. a stable free radical, for the manufacture of a contrast medium for use in the method of the invention.

It will be appreciated that where references are made herein to the limits for esr linewidths these will be the linewidths at imaging conditions, e.g. at the imaged sites. Particularly preferably however the linewidth criteria will be satisfied at the local concentration limits mentioned below.

The contrast medium may contain, besides the paramagnetic material, formulation aids such as are conventional for therapeutic and diagnostic compositions in human or veterinary medicine. Thus the media may for example include solubilizing agents, emulsifiers, viscosity enhancers, buffers, etc. The media may be in forms suitable for parenteral (e.g. intravenous) or enteral (e.g. oral) application, for example for application directly into body cavities having external escape ducts (such as the digestive tract,, the bladder and the uterus), or for injection or infusion into the cardiovascular system. However, solutions, suspensions and dispersions in physiologically tolerable media will generally be preferred. Thus in another aspect the invention also provides a contrast medium for thermographic imaging comprising a physiologically tolerable structurally asymmetric nitroxide stable free radical having a temperature dependent and optionally also a temperature independant transition in its esr spectrum, in solution, suspension or dispersion in a physiologically acceptable medium.

For use in in vivo diagnostic imaging, the contrast medium, which preferably will be substantially isotonic, may conveniently be administered at a concentration sufficient to yield a 1 micromolar to 10 mM concentration of the paramagnetic substance at the image zone; however the precise concentration and dosage will of course depend upon a range of factors such as toxicity, the organ targetting ability of the contrast agent, and administration route. The optimum concentration for the paramagnetic substance represents a balance between various factors. In general concentrations may lie in the range 0.1 to 100 mM, especially 1 to 10 mM, more especially 2 to 5 mM. Compositions for intravenous administration preferably will contain the paramagnetic material at concentrations of 10 to 1000 mM, especially preferably 50 to 500 mM. For ionic materials the concentration will particularly preferably be in the range 50-200 mM, especially 140 to 160 mM and for non-ionic materials 200-400 mM, especially 290-330 mM. For imaging of the urinary tract or the renal system however compositions may perhaps be used having concentrations of for example 10-100 mM for ionic or 20 to 200 mM for non-ionic materials. Moreover for bolus injection, the concentration may conveniently be 0.1 to 100 mM, preferably 5 to 25 mM, and especially preferably 6-15 mM.

The nitroxides in contrast media of the invention will preferably exhibit esr linewidths of less than 1 Gauss (0.1 millitesla), especially preferably less than 100 mG (10 $\mu$T), at concentrations of up to 10 mM, especially at 1 or 2 mM.

As discussed above, non-invasive thermographic imaging is particularly desirable for treatment of malignant tissue by hyperthermia, although it is also of general use in the detection and location of abnormal tissues, and in one particularly preferred embodiment the apparatus of the invention is further provided with sources of directable tissue destroying radiation, e.g. microwave emitters, which may be operated to treat body sites identified as being malignancy locations.

In a further preferred embodiment, the MW emitter used to generate the esr excitation described above can also serve as the radiation source for hyperthermic treatment.

Such sources of directable radiation are preferably provided with movable mounting means so as to be locatable to emit tissue destroying radiation in a selected direction.

In this way the heating effect of the tissue destroying radiation may be monitored by the apparatus of the invention enabling the tissue destroying radiation sources to be so located as to avoid generation of hot spots in healthy tissue and to avoid irradiating tissues which might shadow the malignancy locations and so prevent the temperature increase at such locations from being sufficient. Alternatively, the radiation sources may of course be held static if the apparatus is provided with means for adjusting the position of the body being imaged.

Thus viewed from a yet further aspect the invention provides a process of treating malignant tissue in a body by irradiation with tissue destroying radiation, which method comprises thermographically imaging said body or said malignant tissue therein by the method of the invention and adjusting the direction and/or duration of irradiation of said body by tissue destroying radiation to reduce thermal damage to healthy tissue within said body.

BRIEF DESCRIPTION OF THE INVENTION

Figure 2:
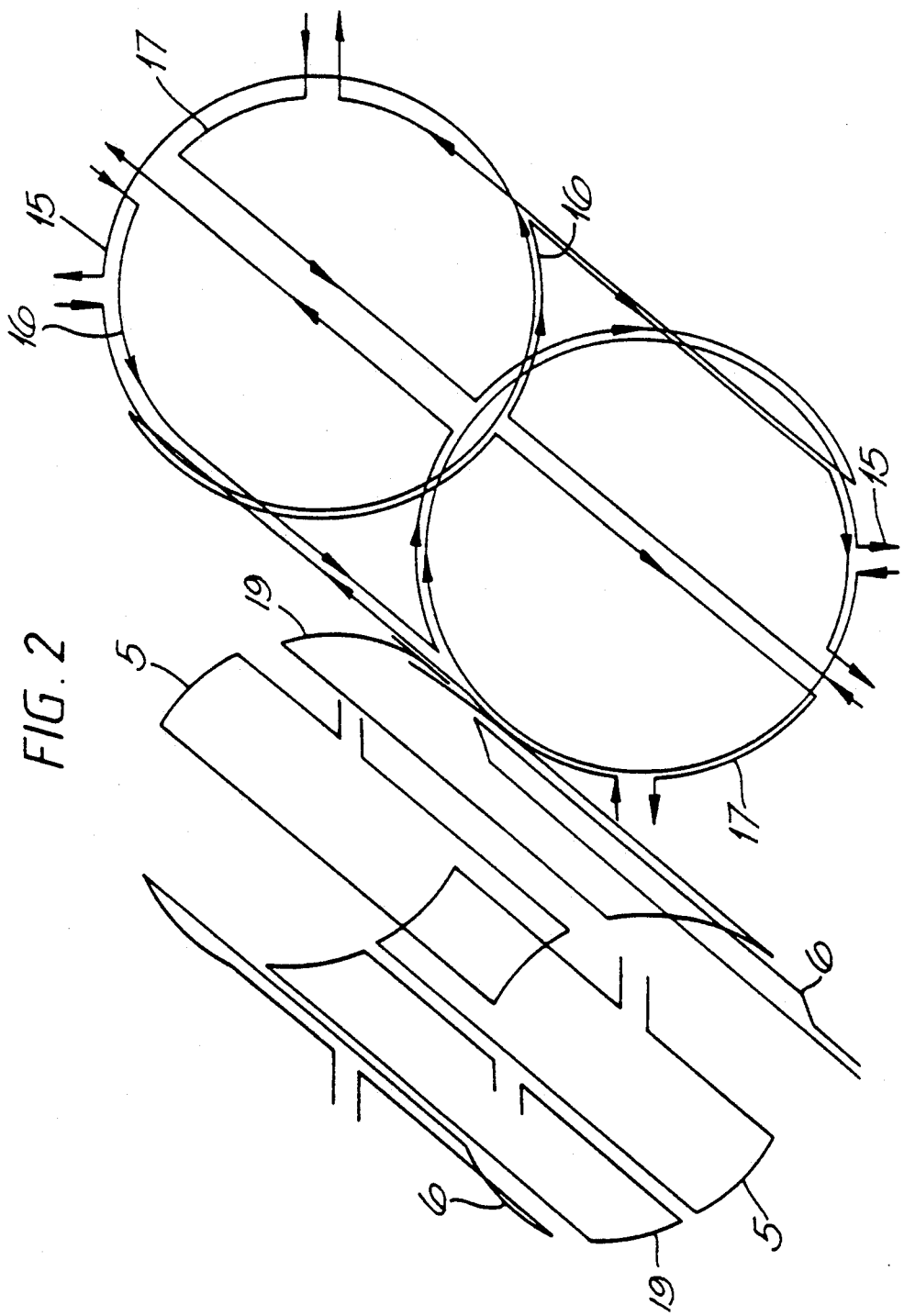

The invention will now be described further by way of example and with reference to the accompanying drawings in which:

FIG. 1 is a schematic perspective drawing of a thermographic imaging apparatus according to the invention; and FIG. 2 is a schematic perspective view of the emitters of the first to third radiation in the apparatus of FIG. 1.

Referring to FIG. 1, there is shown an ESREMRI apparatus 1 having a sample 2, dosed with a paramagnetic contrast medium manufactured according to the invention, placed at the axis of the coils of electromagnet 3. Power from DC supply 4 to the electromagnet 3 enables a primary magnetic field to be generated if the apparatus is to be used in conventional MRI or ESREMRI. For the new method the invention electromagnet 3 is energised if imaging is to be effected in a generated primary magnetic field.

The apparatus is further provided with resonators 5, 6 and 19 for emitting the first, second and third radiations respectively. Resonator 5 is connected to "RF" transceiver 7 powered by power supply 8 and resonator 6 and 19 are connected, for example by waveguides, to "MW" generators 9 and 21 which are powered by power supplies 10 and 20.

"MW" generators 9 and 21 may be arranged to emit "MW" radiation having more than one maximum frequency in order to excite more than one esr transition.

In one particularly preferred embodiment the apparatus of the invention is further provided with source (22) of directable tissue destroying radiation, e.g. microwave emitters, which may be operated to treat body sites identified as being malignancy locations. In a further preferred embodiment, the MW EMITTER used to generate the esr excitation described above can also serve as the radiation source for hyperthermic treatment.

The frequency selection, bandwidth, pulse duration and pulse timing of the first, second and third radiations emitted by resonators 5, 6 and 19 are controlled by control computer 11 and interface module 18 which also control the energisation or deenergisation of electromagnet 3.

Computer 11 also controls the power supply from power sources 12, 13 and 14 to the three pairs of Helmholtz coils 15, 16 and 17 which are shown in further detail in FIG. 2. The coils of coil pair 15 are coaxial with the coils of electromagnet 3 and the saddle coils of coil pairs 16 and 17 are arranged symmetrically about that axis, the Z axis, with their own axes mutually perpendicular and perpendicular to the Z axis. Coil pairs 15, 16 and 17 are used to generate the magnetic field gradients that are superimposed on the uniform field at various stages of the imaging procedure, e.g. in two-dimensional Fourier transform imaging, and the timing sequence for operation of the coil pairs and for operation of the "MW" generator and the "RF" transceiver is controlled by computer 11 and interface module 18.

The apparatus may also be provided with decoupler comprising a further "RF" resonator connected to an "RF" transmitter and a power supply (not shown) and controlled by computer 11. The decoupler may be operated to emit a further radiation at a frequency selected to excite the nuclear spin transition in non-zero spin nuclei in the contrast agent.

In operation the power supply to electromagnet 3 may be switched on or off depending on whether the apparatus is to be operated at ambient or higher magnetic fields. The sample 2, e.g. a patient, is placed within the coil cavity and the imaging procedure is begun.

Interface module 18 activates the power supply to coil pair 15 for a short time period during which DC current flowing through the coils of coil pair 15 in opposite directions about the Z axis results in an approximately linear field gradient in the Z direction being imposed on the ambient field.

Within the time period for which coil pair 15 is energized, interface module 18 activates "RF" transceiver 7 to cause resonator 5 to emit an "RF" pulse, e.g. a 90° pulse, to excite the nmr transition of those resonating nuclei (generally protons) whose Larmor frequencies correspond to the frequency band of the "RF" pulse. The duration, intensity, band width and central frequency of the "RF" pulse may be selected by computer 11.

Effectively the "RF" pulse serves to excite the MR transition of the selected non-zero nuclear spin isotope (generally water protons) within a cross-section (the image zone) of the sample that is transverse to but has thickness in the Z direction.

On termination of the "RF" pulse, current in coil pair 15 is also terminated and after a very short delay interface module 18 energizes coil pair 16 to provide a field gradient in the Y direction for a short time period. This is termed the phase encoding gradient as the field gradient causes the Larmor frequency for the resonating nuclei to vary linearly across the image zone in the Y direction for the period that coil pair 15 is energized. With the removal of the perturbation of the Larmor frequencies on termination of the phase encoding gradient, the oscillation frequencies of the contributions to the FID signal from different source areas of the image zone return to being substantially the same, but the phases of such contributions are shifted to an extent dependant on the location of the particular source area along the Y direction.

After terminating current in coil pair 16, the interface module 18 then energizes coil pair 17 to provide a field gradient (the read gradient) in the X direction, and reactivates "RF" transceiver 7 to detect the FID signal from the sample.

The FID signal is assumed to arise from the transverse magnetization of the nuclear spin system within the image zone since the MR transition was excited by the "RF" pulse for resonating nuclei in this zone only. As described above, the intensity of the FID signal as a function of time contains encoded information regarding the distribution of the resonating nuclei in the image zone in the X and Y directions respectively.

The FID signal intensity falls off exponentially with time as the system dephases and the period for which the read gradient is imposed and the transceiver 7 detects the FID signal from the sample is generally very short, for example of the order of milliseconds.

To generate an MR image of the image zone it is necessary to repeat the pulse and detection sequence for many further times, e.g. 64–1024 times, each time generating phase encoding gradients of different magnitude or duration. Often, to produce a good S/N ratio, signals for several, e.g. 2–4, identically performed sequences will be summed. FID signals for each set of sequences are transformed by the computer 11 using a standard two-dimensional Fourier transform algorithm to produce the desired spatial images of the image zone.

In conventional MRI, after termination of the only or the last FID signal detection period in a pulse and detection sequence and before the subsequent imposition of the slice selection gradient and emission of the initiating RF pulse of the next sequence, it has been necessary to wait for a delay period, generally of the order of seconds, until the resonating nuclei have relaxed to near equilibrium in order to build up sufficient longitudinal magnetization for the FID signal following the new RF pulse to be sufficiently strong to give an acceptable S/N ratio.

However, in ESREMRI, the delay period following the only or the last detection period may be reduced by the use of the amplified nuclear population difference resulting from the coupling between the electron MR and nuclear MR transitions. Alternatively put, by irradiating the sample with "MW" radiation before the or each "RF" pulse, amplification of the nuclear spin state population difference relative to the population difference at equilbrium in the absence of "MW" irradiation may be achieved thus enabling the FID signal to be enhanced. Thus for example in at least the period between termination of the last read gradient for each pulse sequence and the emission of the initiating "RF" pulse of the next sequence, for example for a period of about 10 ms to 100 ms, interface module 18 activates "MW" generator 9 or 21 to cause the sample to be irradiated with "MW" radiation of a selected power and of a central frequency corresponding to the Larmor frequency of a temperature independent or a temperature dependent esr transition of the paramagnetic centre in the contrast agent in the sample; either CW radiation or, preferably, a train of radiation pulses.

The selection of the "MW" frequency and power is made by computer 11 which also transforms the detected FID signals in the manner described to yield an MRI image indicative of the thermal distribution across the image zone.

To minimise field inhomogeneities, the sample cavity of the apparatus of the invention should preferably be provided with shielding (not shown), conveniently shielding which may be moved into place between the electromagnet 3 and the Helmholtz coils 15, 16 and 17 and/or permanent shielding between coils 15, 16 and 17 and the electronic control equipment and power sources (4, 7–14, 18).

I claim:

1. A method of determining temperature of at least one site of a body containing a paramagnetic substance having a first electron spin resonance transition, the central frequency of which is temperature dependent, said method comprising exposing said body to a first radiation of a frequency selected to excite nuclear spin transitions in selected nuclei in said body, exposing said body to a second radiation of a frequency selected to excite said electron spin resonance transition, said second radiation being at the central frequency of said electron spin resonance transition at a selected reference temperature, detecting free induction decay signals from the body, and from said free induction decay signals generating a signal indicative of the temperature at said site.

2. A method as claimed in claim 1 wherein said paramagnetic substance has a second electron spin resonance transition, the central frequency of which is temperature independent, said method further comprising exposing said body to a third radiation of a frequency selected to excite said second electron spin resonance transition.

3. A method as claimed in claim 2 wherein said body is exposed to a series of pulse sequences of said first radiation and is exposed to said second radiation during a first set of said sequences and to said third radiation during a second set of said sequences, said method comprising generating said signal indicative of temperature from the free induction decay signal detected in said first and second sequences.

4. A method as claimed in claim 1 wherein exposure of said body to said second and third radiations is effected at at least two different power levels.

5. A method as claimed in claim 2 comprising the following steps:
   a) distributing the paramagnetic substance within said body;
   b) exposing said body to a series of pulse sequences of said first radiation;
   c) exposing said body during a first set of said sequences to said second radiation at a first selected power level;
   d) detecting free induction decay signals from said body in said first set of sequences;
   e) exposing said body during a second set of said sequences to a third radiation of a frequency selected to excite said second electron spin resonance transition at said first selected power level;
   f) detecting free induction decay signals from said body in said second set of sequences;
   g) exposing said body during a third set of sequences to said second radiation at a second selected power level;
   h) detecting free induction decay signals from said body in said third set of sequences;
   i) exposing said body during a fourth set of sequences to said third radiation at said second selected power level;
   j) detecting free induction decays signals from said body in said fourth set of sequences;
   k) exposing said body during a fifth set of said sequences to a fourth radiation of a frequency selected to excite said first electron spin resonance transition, said fourth radiation being at the central frequency of said first electron spin resonance transition at a second selected reference temperature and said fourth radiation being at said first selected power level;
   l) detecting free induction decay signals from said body in said fifth set of sequences; and
   m) generating from the free induction signals detected in steps (d), (f), (h), (j) and (l) the signal indicative of temperature.

6. A method as claimed in claim 2 comprising the following steps:
   a) distributing the paramagnetic substance within said body;
   b) exposing said body to a series of pulse sequences of said first radiation;
   c) exposing said body during a first set of said sequences to said second radiation at a first selected power level;
   d) detecting free induction decay signals from said body in said first set of sequences;
   e) exposing said body during a second set of said sequences to a third radiation of a frequency selected to excite said second electron spin resonance transition at said first selected power level;
   f) detecting free induction decay signals from said body in said second set of sequences;
   g) exposing said body during a third set of sequences to said second radiation at a second selected power level;
   h) detecting free induction decay signals from said body in said third set of sequences;
   i) exposing said body during a fourth set of sequences to said third radiation at said second selected power level;
   j) detecting free induction decays signals from said body in said fourth set of sequences;
   k) exposing said body during a fifth set of said sequences to a fourth radiation of a frequency selected to excite said first electron spin resonance transition, said fourth radiation being at the central frequency of said first electron spin resonance transition at a second selected reference temperature and said fourth radiation being at said first selected power level;
   l) detecting free induction decay signals from said body in said fifth set of sequences; and
   m) generating from the free induction signals detected in steps (d), (f), (h), (j) and (l) the signal indicative of temperature.

7. A method as claimed in claim 1 further comprising exposing said body to a further radiation of a frequency selected to excite said first electron spin resonance transition, said further radiation being at the central frequency of said first electron spin resonance transition at a second selected reference temperature.

8. A method as claimed in claim 1 wherein said body is a human or animal body and said paramagnetic substance is a physiologically tolerable material administered to said body.

9. A method as claimed in claim 1 which further comprises generating free induction decay signals indicative of the temperature at a plurality of sites in said body, and generating therefrom an image of temperature distribution in said body.

10. A temperature determining apparatus comprising a first radiation source means which emits pulse sequences of a first radiation of a frequency selected to excite nuclear spin transitions in a body, means for detecting free induction decay signals from said selected nuclei, a second and third radiation source means which respectively emit during selected said pulse sequences second and third radiations of frequencies selected to excite in a paramagnetic substance present in said body one or more electron spin transitions coupled to the nuclear spin transitions of at least some of said nuclei, and generating means arranged to generate a signal indicative of the temperature at one or more sites of said body from the free induction decay signals detected by said means for detecting during pulse sequences in which said body is exposed to said radiations.

11. An apparatus as claimed in claim 10 further comprising a fourth radiation source means which emits a fourth radiation of a frequency selected to excite in a paramagnetic substance present in said body an electron spin transition coupled to the nuclear spin transition of at least some of said nuclei.

12. An apparatus as claimed in claim 11 further comprising a fifth radiation source means which emits during selected said pulse sequences a fifth radiation, said second, third, fourth and fifth radiations being of selected frequencies to excite in a paramagnetic substance present in said body at least two electron spin transitions coupled to the nuclear spin transitions of at least some of said nuclei.

13. An apparatus as claimed in claim 12 wherein said second, third, fourth and fifth radiation source means are provided with control means which permit selection of the timing, power and frequency of said second and higher radiations.

14. An apparatus as claimed in claim 10 further comprising means for providing magnetic resonance image of said body.

15. An apparatus as claimed in claim 10 further provided with means for generating a source of directable tissue destroying radiation responsive to the signal indicative of the temperature at one or more sites of said body.

16. A process for treating malignant tissue in a body by irradiation with tissue destroying radiation, which process comprises thermographically imaging said body or said malignant tissue therein by a method which comprises administering to said body a paramagnetic substance having a first electron spin resonance transition, the central frequency of which is temperature dependent, exposing said body to a first radiation of a frequency selected to excite nuclear spin transitions in selected nuclei in said body, exposing said body to a second radiation of a frequency selected to excite said electron spin resonance transition, said second radiation being at the central frequency of said electron spin resonance transition at a selected reference temperature, detecting free induction signals from said body, generating from said free induction decay signals an image indicative of the temperature in said body, and adjusting the direction of irradiation of said body by said tissue destroying radiation to reduce thermal damage to healthy tissue within said body.

17. A process of treating malignant tissue in a body by irradiation with tissue destroying radiation, which process comprises thermographically imaging said body or said malignant tissue therein by a method which comprises administering to said body a paramagnetic substance having a first electron spin resonant transition, the central frequency of which is temperature dependent, exposing said body to a first radiation of a frequency selected to excite nuclear spin transitions in selected nuclei in said body, exposing said body to a second radiation of a frequency selected to excite said electron spin resonance transition, said second radiation being at the central frequency of said electron spin resonance transition at a selected reference temperature, detecting free induction signals from said body, generating from said free induction decay signals an image indicative of the temperature in said body, said adjusting the duration of irradiation of said body by said tissue destroying radiation to reduce thermal damage to healthy tissue within said body.

18. A process of treating malignant tissue in a body by irradiation with tissue destroying radiation, which process comprises thermographically imaging said body or said malignant tissue therein by adjusting the direction and duration which comprises administering to said body a paramagnetic substance having a first electron spin resonant transition, the central frequency of which is temperature dependent, exposing said body to a first radiation of a frequency selected to excite nuclear spin transitions in selected nuclei in said body, exposing said body to a second radiation of a frequency selected to excite said electron spin resonance transition, said second radiation being at the central frequency of said electron spin resonance transition at a selected reference temperature, detecting free induction signals from said body, generating from said free induction decay signals an image indicative of the temperature in said body, and adjusting the direction and duration of irradiation of said body by said tissue destroying radiation to reduce thermal damage to healthy tissue within said body.

* * * * *